(12) United States Patent
Britva et al.

(10) Patent No.: US 11,278,745 B2
(45) Date of Patent: Mar. 22, 2022

(54) SONOTRODE

(71) Applicant: Alma Lasers Ltd., Caesarea (IL)

(72) Inventors: Alexander Britva, Migdal Ha'Emek (IL); Alexander Dverin, Netanya (IL); Yevgeny Pens, Kiryat Bialik (IL); Joseph Lepselter, Nordiya (IL); Ziv Karni, Kfar Shmaryahu (IL); Shahar Tsurgil, HaHotrim (IL); Ohad Toledano, Tel Aviv (IL)

(73) Assignee: ALMA LASERS LTD.

( * ) Notice: Subject to any disclaimer, the term of this patent is extended or adjusted under 35 U.S.C. 154(b) by 662 days.

(21) Appl. No.: 16/081,966

(22) PCT Filed: Mar. 3, 2017

(86) PCT No.: PCT/IB2017/051253
§ 371 (c)(1),
(2) Date: Sep. 4, 2018

(87) PCT Pub. No.: WO2017/149506
PCT Pub. Date: Sep. 8, 2017

(65) Prior Publication Data
US 2019/0091490 A1  Mar. 28, 2019

Related U.S. Application Data

(60) Provisional application No. 62/302,875, filed on Mar. 3, 2016.

(51) Int. Cl.
*A61N 7/00* (2006.01)
*A61B 17/32* (2006.01)

(52) U.S. Cl.
CPC .... *A61N 7/00* (2013.01); *A61B 2017/320098* (2017.08); *A61N 2007/0008* (2013.01); *A61N 2007/0034* (2013.01)

(58) Field of Classification Search
CPC .............. A61N 7/00; A61N 2007/0034; A61N 2007/0008; A61B 2018/00464
See application file for complete search history.

(56) References Cited

U.S. PATENT DOCUMENTS

2011/0213279 A1\* 9/2011 Britva ...................... A61N 7/00
601/2

FOREIGN PATENT DOCUMENTS

| KR | 10-1358374 | 4/2012 |
| WO | WO92/09238 | 6/1992 |

OTHER PUBLICATIONS

Communication Pursuant to Rules 161(1) and 162 EPC, European Patent Office, Application No. 17716628.7-1115, dated Oct. 11, 2018.
Messulam, Amendment and Response to Communication Pursuant to Rules 161(1) and 162 EPC, Application No. 17716628.7-1115, dated Apr. 17, 2019.

(Continued)

*Primary Examiner* — Jason M Ip
(74) *Attorney, Agent, or Firm* — Fresh IP PLC; Clifford D. Hyra; Aubrey Y. Chen (57) ABSTRACT

Disclosed are methods and devices for treatment of subcutaneous fat by simultaneously transdermally inducing both ultrasonic transverse vibrations and ultrasonic longitudinal vibrations in subcutaneous tissue, for example for reduction of subcutaneous fat.

16 Claims, 3 Drawing Sheets

(56) References Cited

OTHER PUBLICATIONS

Notification of Reason for Rejection, Japan Patent Office, Application No. 2018-545849, dated Jan. 12, 2021.
Notice of Submission of Opinions, Korean Intellectual Property Office, Application No. 10-2018-7026238, dated Feb. 2, 2021.

* cited by examiner

SONOTRODE

RELATED APPLICATION

The present application gains priority from U.S. Provisional Patent Application 62/302,875 filed 3 Mar. 2016, which is included by reference as if fully set-forth herein and is also attached hereto in its entirety as an Appendix.

FIELD AND BACKGROUND OF THE INVENTION

The invention, in some embodiments, relates to the field of treatment of body tissue with acoustically-delivered energy and more particularly, but not exclusively, to methods and devices for treatment of subcutaneous fat by simultaneously transdermally inducing both ultrasonic transverse vibrations and ultrasonic longitudinal vibrations in subcutaneous tissue thereby acoustically delivering energy through the skin, for example for reduction of subcutaneous fat by applying ultrasonic vibrations to a skin surface.

In the art it is known to apply ultrasonic vibrations to a skin surface to transdermally induce ultrasonic vibrations to acoustically deliver energy to subcutaneous tissue such as a subcutaneous fat layer to damage adipocytes, for example in the field of body sculpting.

Application of ultrasonic vibrations to a surface is typically performed by a device 10 (see FIG. 1) that includes a proximal ultrasonic transducer 12 for generation of ultrasonic longitudinal vibrations (e.g., a Langevin-type transducer comprising a stack of piezoelectric elements) having a proximal face 14 functionally associated with an acoustic reflector 16 and a distal face 18 and a distal sonotrode 20 having a proximal face 22, a distal end 24 defining a working face 26 that constitutes an acoustic radiative surface and a sonotrode axis 28, where the proximal face 22 of the sonotrode 20 is acoustically coupled to the distal face 18 of the ultrasonic transducer 12.

Figure 1:
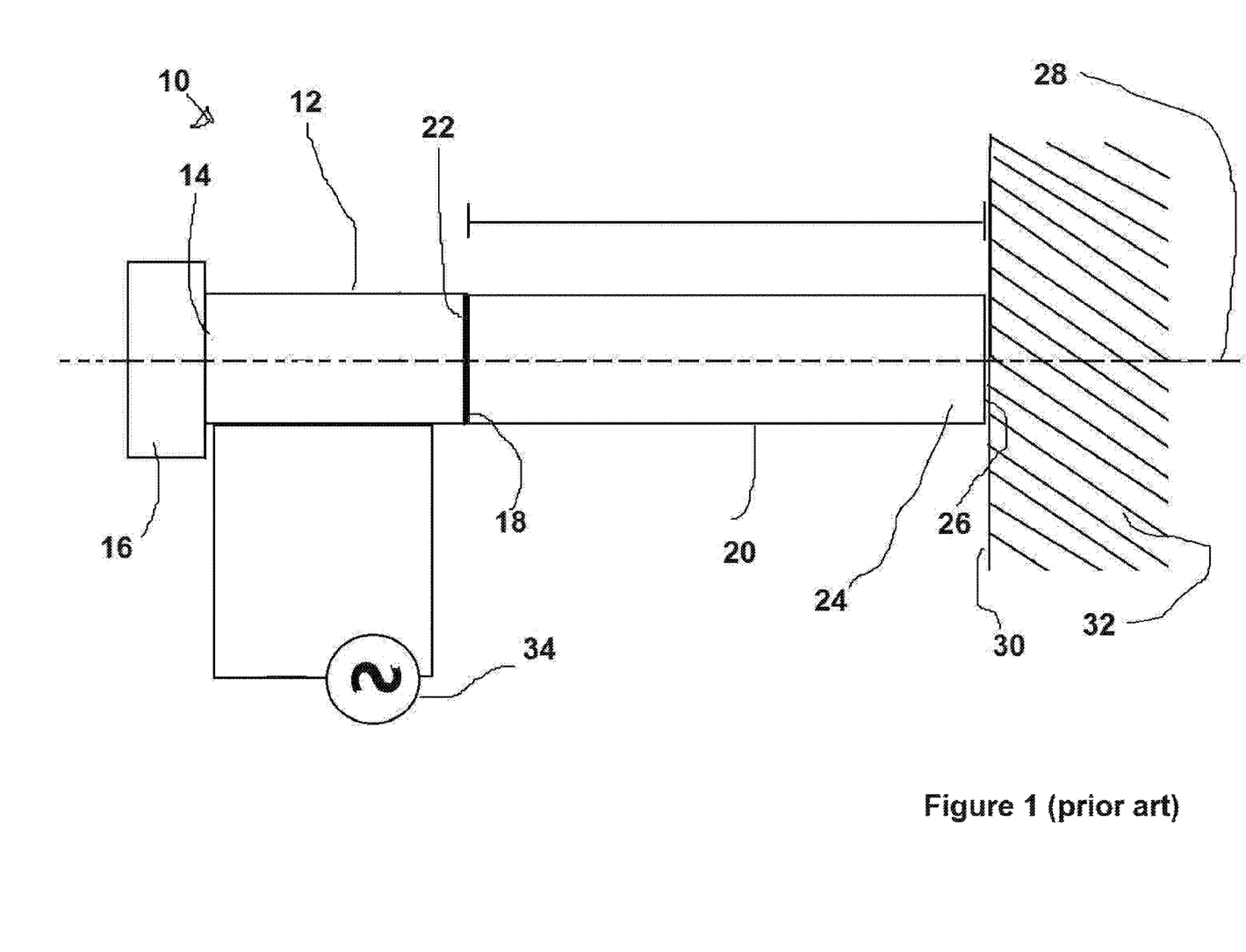
FIG. 1 (prior art) schematically depicts a device for application of ultrasonic vibrations into a medium through a surface of the medium.

For use, while the working face 26 of the sonotrode 20 is acoustically coupled to a surface 30 of a medium 32 (e.g., by direct contact or by indirect contact through a coupling substance, e.g., a liquid or gel), an alternating current (AC) oscillating at an ultrasonic driving frequency is supplied from an ultrasound power supply 34 to drive the ultrasonic transducer 12. The piezoelectric elements of the ultrasonic transducer 12 expand and relax at the driving frequency in response to the oscillations of the AC potential, thereby generating ultrasonic longitudinal vibrations with the frequency of the driving frequency. The generated ultrasonic longitudinal vibrations propagate in parallel with the axis 28 through the sonotrode 20 from the proximal face 22 to the working face 26. The working face 26 applies the ultrasonic longitudinal vibrations to the surface 30, inducing ultrasonic longitudinal vibrations in the medium 32.

Figure 2A:
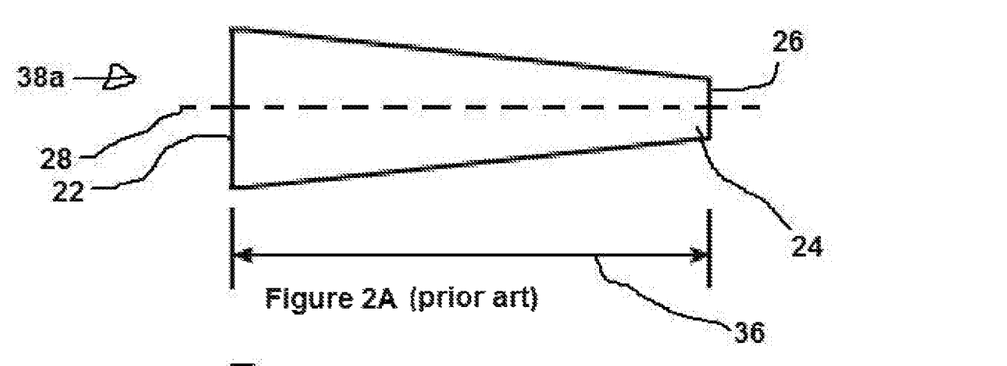
FIG. 2A linear taper sonotrode.
Figure 2B:
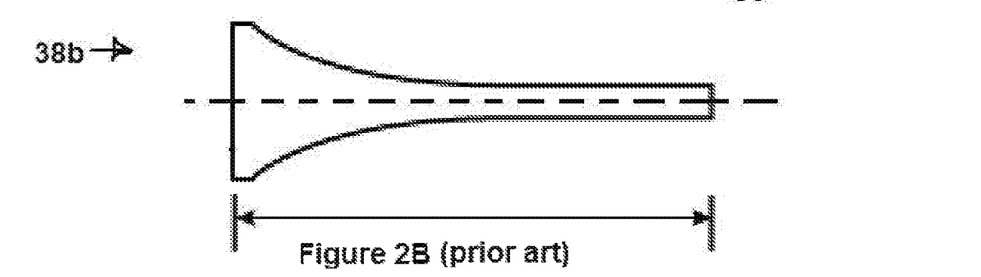
FIG. 2B exponential taper sonotrode.
Figure 2C:
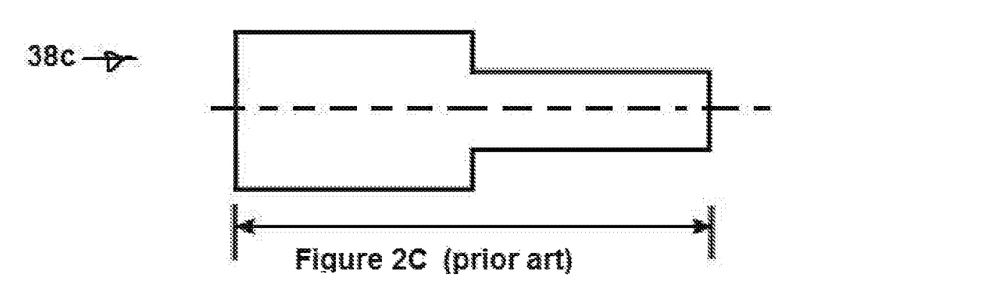
FIG. 2C stepped taper sonotrode.

For practical use it is advantageous to configure a sonotrode to function as an acoustic amplitude transformer (also called a horn) that increases the amplitude of the ultrasonic longitudinal vibrations (i.e., the maximal displacement of distal working face 26) from being relatively small at the proximal face 22 of the sonotrode 20 to substantially larger at working face 26, typically to between 10 and 150 micrometers. Such configuration includes that the sonotrode tapers from a large cross section proximal end 22 to a small cross section working face 26 and that the total length 36 of the sonotrode (from proximal face 22 to working face 26) is an integral multiple of $\lambda L/2$, $\lambda L$ being the wavelength of the ultrasonic longitudinal vibrations in the sonotrode which is dependent on the driving frequency and on the longitudinal speed of sound along the axis 28 so that the sonotrode functions as a half-wavelength resonator. The most popular such acoustic amplitude transformer configurations are schematically depicted in side cross section in FIG. 2: FIG. 2A a linear taper sonotrode 38a, FIG. 2B an exponential taper sonotrode 38b, and FIG. 2C a stepped taper sonotrode 38c.

When a sonotrode 20, 38a, 38b or 38c, as depicted in FIG. 1, 2A, 2B or 2C respectively is used, the ultrasonic vibrations in the sonotrode and that are induced in a medium are predominantly, if not entirely, longitudinal vibrations that propagate collinearly with the axis 28 of the sonotrode. The biological effects of energy transdermally delivered by ultrasonic longitudinal vibrations primarily arise from heating of tissue, especially heating of the dermis.

Figure 2D:
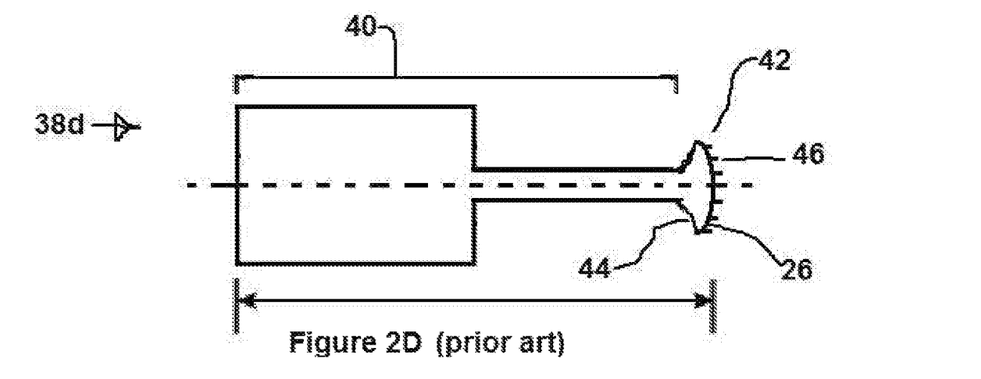
FIG. 2D mushroom sonotrode according to US 2011/0213279.

In patent publication US 2011/0213279 which is included by reference as if fully set-forth herein, some of the Inventors disclosed a "mushroom-shaped" sonotrode. In FIG. 2d, such a mushroom-shaped sonotrode 38d is schematically depicted in side cross section having a tapering stem 40 that functions as an acoustic amplitude transformer as described above (particularly sonotrode 38c depicted in FIG. 2C) and a broader cap 42. Cap 42 is lenticular, in side cross section resembling a lens having a curved back side 44 and a convex working face 26. Working face 26 of sonotrode 38d also includes concentric circular transverse-wave transferring ridges 46.

As detailed in US 2011/0213279, a sonotrode such as 38d is operative to transdermally induce, depending on the value of the driving frequency, either ultrasonic longitudinal vibrations or ultrasonic transverse vibrations in subcutaneous tissue when the working face 26 is acoustically coupled with skin.

Without wishing to be held to any one theory, it is currently believed that with some driving frequencies the ultrasonic longitudinal vibrations generated by an ultrasonic transducer 12 preferentially propagate in parallel with the axis 28 of mushroom-shaped sonotrode such as 38d from the proximal face 22 to the working face 26. These ultrasonic longitudinal vibrations primarily lead to ultrasonic longitudinal vibrations of the sonotrode 38d, which are applied by working face 26 to a skin surface acoustically coupled with working face 26, transdermally inducing ultrasonic longitudinal vibrations in the subcutaneous tissue.

However, with some other different driving frequencies the ultrasonic longitudinal vibrations generated by an ultrasonic transducer 12 preferentially produce ultrasonic shear wave vibrations in the cap 42 of sonotrode 38d, the ultrasonic shear wave vibrations being perpendicular to the longitudinal vibrations in the stem 40, that is to say, a greater proportion of the energy transferred by the transducer 12 into the sonotrode 38d is in ultrasonic shear wave vibrations in the cap 42 perpendicular to axis 28 rather than ultrasonic longitudinal vibrations parallel or collinear with axis 28. As a result, working face 26 substantially vibrates transversely, presumably alternately increasing and decreasing in diameter. When the vibrating working face 26 is applied to a skin surface, the ultrasonic shear wave vibrations induce ultrasonic transverse vibrations in the subcutaneous tissue by virtue of the convex shape of working face 26 and by virtue of the concentric circular transverse-wave transferring ridges 46 that can be considered as physically moving the skin and tissue transversely.

A device including a sonotrode such as 38d provides two modes of operation that are advantageously serially activated:

at a first driving frequency that is related to the wavelength λL for which the sonotrode 38*d* is configured to act as an acoustic amplitude transformer, a first "hot" or "longitudinal" mode where the energy transdermally delivered to subcutaneous tissue through the working face 26 is primarily by ultrasonic longitudinal vibrations that are perpendicular to the skin surface; and at a second driving frequency different from the first driving frequency, a second "cold" or "transverse" mode where the energy transdermally delivered to subcutaneous tissue through the working face 26 is primarily by ultrasonic transverse vibrations that are parallel to the skin surface. As described in US 2011/0213279, relatively low-energy "cold" ultrasonic transverse waves disrupt adipocytes, apparently by repeatedly stretching the cell membranes and then allowing these to relax, yet cause substantially no collateral damage to surrounding non-adipose tissue.

In some preferred embodiments described in US 2011/0213279, ultrasonic longitudinal vibrations of the first mode and ultrasonic shear wave vibrations of the second mode are alternately applied through a mushroom-shaped sonotrode such as 38*d* described above. The ultrasonic longitudinal vibrations are applied by the working face to the skin surface (typically for a duration of about 5 seconds) to transdermally induce ultrasonic longitudinal waves that heat subcutaneous tissue such as the dermis. Subsequently ultrasonic shear wave vibrations are applied by the working face to the skin surface (typically for a duration of about 15 seconds) to induce ultrasonic transverse vibrations to disrupt the adipocytes. Because of the preceding heating by the ultrasonic longitudinal vibrations, the ultrasonic transverse vibrations penetrate more deeply and/or more effectively and/or a greater fraction of the energy penetrates to a given depth of the adipose tissue and/or the heated tissue has improved energy-absorbing properties.

Although highly effective in the field of body sculpting, a sonotrode such as described in US 2011/0213279 is sometimes considered less than ideal for some uses because the shear wave vibrations are not applied continuously, because of the added complexity required for generating and switching between two different driving frequencies and because if a user moves the working face over different portions of a treated subjects too quickly, the results of a treatment might be considered less than ideal.

SUMMARY OF THE INVENTION

The invention, in some embodiments, relates to the treatment of body tissue with energy and more particularly, but not exclusively, to methods and devices for treatment of subcutaneous fat by simultaneously transdermally inducing both ultrasonic transverse vibrations and ultrasonic longitudinal vibrations in subcutaneous tissue, for example for reduction of subcutaneous fat.

According to an aspect of some embodiments of the invention there is provided a device suitable for treating subcutaneous adipose tissue, comprising:
a. an ultrasonic transducer for generation of ultrasonic vibrations having a proximal face and a distal face; and
b. a sonotrode including a narrower proximal stem portion defining a sonotrode axis and a broader distal cap portion
wherein the stem portion has a distal end and bears a proximal face of the sonotrode, the sonotrode acoustically coupled to the distal face of the ultrasonic transducer through the proximal face of the sonotrode,
wherein the cap portion has a proximally-facing back side, a distal working face of the sonotrode and a periphery,
wherein the distal end of the stem portion meets the back side of the cap portion,
wherein where the distal end of the stem portion meets the back side of the cap portion a cross sectional area of the cap portion perpendicular to the sonotrode axis is not less than 4 times greater than a cross sectional area of the distal end of the stem portion perpendicular to the sonotrode axis; and
wherein said sonotrode is configured as an acoustic amplitude transformer for a selected ultrasonic frequency.

According to an aspect of some embodiments of the invention, there is also provided a method of transdermally treating subcutaneous fat comprising:
 i. providing a device according to the teachings herein, wherein the ultrasonic transducer is functionally associated with an ultrasound power supply;
 ii. for a treatment event having a duration, maintaining the working face acoustically coupled with a skin surface while the ultrasound power supply is activated to supply a driving current having the selected ultrasonic frequency to the ultrasonic transducer,
thereby simultaneously transdermally inducing both:
  ultrasonic longitudinal vibrations sufficient to convey sufficient energy to substantially heat subcutaneous tissue; and
  ultrasonic transverse vibrations in subcutaneous tissue to convey sufficient energy to disrupt adipocytes in the subcutaneous tissue.

According to an aspect of some embodiments of the invention there is also provided a method of transdermally treating subcutaneous fat, comprising:
 i. providing a plate having a working face;
 ii. acoustically coupling the plate through the working face with a skin surface; and
 iii. forming ultrasonic-frequency cylindrical plate waves in the plate with a perpendicular line source,
wherein the cylindrical plate waves formed in the plate lead to ultrasonic flexural vibrations of the plate that transdermally induce ultrasonic transverse waves in subcutaneous tissue, thereby treating subcutaneous fat. In some embodiments, the ultrasonic transverse waves disrupt adipocytes in the subcutaneous tissue. In some embodiments, the perpendicular line source is an ultrasonic longitudinal wave.

In some embodiments, the method further comprises simultaneously with the transdermally inducing ultrasonic transverse waves in subcutaneous tissue, transdermally inducing ultrasonic longitudinal waves in subcutaneous tissue. In some embodiments, the ultrasonic longitudinal waves heat the subcutaneous tissue. In some embodiments, the ultrasonic transverse waves are induced in the subcutaneous tissue with an ultrasonic longitudinal wave that propagates perpendicularly to the plate and constitutes the perpendicular line source.

Typically, the method is non-invasive, that is to say the skin surface remains intact, and is not punctured or otherwise penetrated. In some embodiments, the method is a non-surgical method, performed without breaking the skin. Embodiments of the method are performed by any suitable person, including medical personnel but typically aesthetic technicians such as beauticians.

U.S. Provisional Patent Application 62/302,875 filed 3 Mar. 2016, from which the instant application gains priority, is attached hereto in its entirety as an Appendix. The Appendix is an integral part of the application.

Unless otherwise defined, all technical and scientific terms used herein have the same meaning as commonly understood by one of ordinary skill in the art to which the invention pertains. In case of conflict, the specification, including definitions, will control.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise."

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIGS. 2A, 2B, 2C and 2D (prior art) schematically depict different sonotrodes configured to function as acoustic amplitude transformers.

DESCRIPTION OF SOME EMBODIMENTS OF THE INVENTION

The invention, in some embodiments, relates to the treatment of body tissue with energy and more particularly, but not exclusively, to methods and devices for treatment of subcutaneous fat by simultaneously transdermally inducing both ultrasonic transverse vibrations and ultrasonic longitudinal vibrations in subcutaneous tissue, thereby acoustically delivering energy through the skin to treat subcutaneous fat, by applying ultrasonic vibrations to a skin surface The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

As discussed above, in US 2011/0213279 are disclosed methods and devices for serially transdermally inducing ultrasonic transverse vibrations and ultrasonic longitudinal vibrations in a volume of subcutaneous tissue thereby acoustically conveying energy through the skin to treat subcutaneous fat. Energy conveyed by the ultrasonic transverse vibrations selectively and effectively disrupts adipocytes in the volume of tissue, while the energy conveyed by the ultrasonic longitudinal vibrations heats subcutaneous tissue, amplifying the efficacy of the ultrasonic transverse vibrations. Although highly effective in the field of body sculpting, a sonotrode such as described in US 2011/0213279 is sometimes considered less than ideal for some uses because the ultrasonic shear wave vibrations that induce transverse vibrations in the tissue are not applied continuously, because of the added complexity required for generating and switching between two different driving frequencies and because if a user moves the working face over different portions of a treated subject too quickly, the results of a treatment might be considered less than ideal.

Herein are disclosed methods and devices for treatment of subcutaneous fat by simultaneously transdermally inducing both ultrasonic transverse vibrations and ultrasonic longitudinal vibrations in subcutaneous tissue, thereby acoustically delivering energy through the skin to treat subcutaneous fat, by applying ultrasonic vibrations to a skin surface, for example for reduction of subcutaneous fat.

According to an aspect of some embodiments of the teachings herein, there is provided a device suitable for treating subcutaneous adipose tissue, comprising:

a. an ultrasonic transducer for generation of ultrasonic vibrations having a proximal face and a distal face; and
b. a sonotrode including a narrower proximal stem portion defining a sonotrode axis and a broader distal cap portion wherein the stem portion has a distal end and bears a proximal face of the sonotrode, the sonotrode acoustically coupled to the distal face of the ultrasonic transducer through the proximal face, wherein the cap portion has a proximally-facing back side, a distal working face of the sonotrode and a periphery, wherein the distal end of the stem portion meets the back side of the cap portion, wherein where the distal end of the stem portion meets the back side of the cap portion the cross sectional area of the cap portion perpendicular to the sonotrode axis is not less than 4 times greater than the cross sectional area of the distal end of the stem portion perpendicular to the sonotrode axis; and wherein the sonotrode is configured to function as an acoustic amplitude transformer for a selected ultrasonic frequency.

Figure 3:
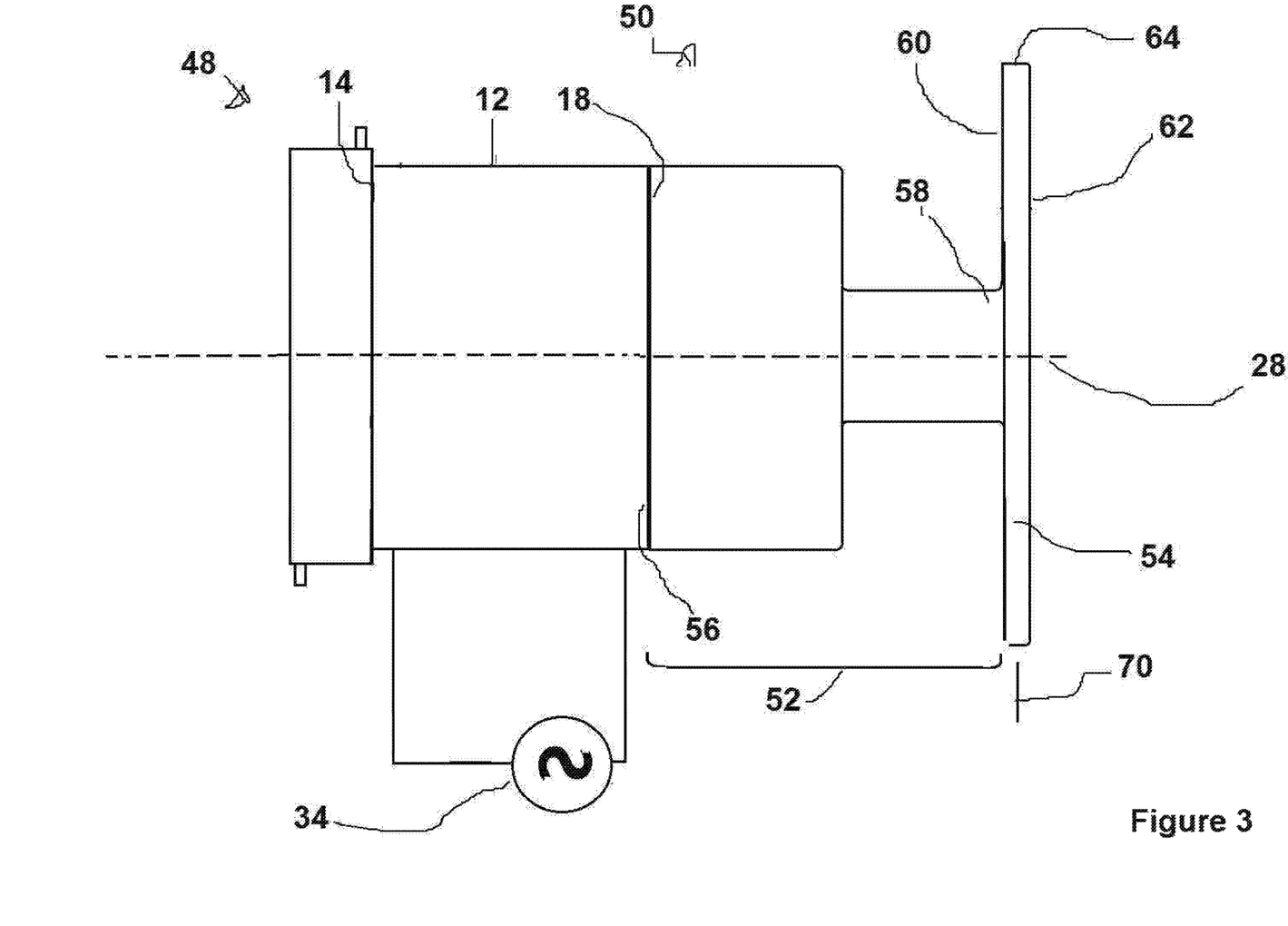
FIG. 3 schematically depicts an embodiment of a device according to the teachings herein.

In FIG. 3, an embodiment of a device according to the teachings herein, device 48 is schematically depicted. A device 48 according to the teachings herein was actually constructed, tested and proved to successfully treat subcutaneous fat, see the reproductions of the photomicrographs on the last page of the Appendix. Device 48 includes an ultrasonic transducer 12 and a sonotrode 50.

Ultrasonic transducer 12 has a proximal face 14 and a distal face 18. Ultrasonic transducer 12 is a Langevin-type prestressed (at between 45 N/m to 100 N/m) transducer that includes a stack of four 6 mm diameter disks, configured to produce ultrasonic longitudinal frequencies of between 58 kHz to 60 kHz.

Sonotrode 50 includes a proximal stem portion 52 defining a sonotrode axis 28 and a distal cap portion 54. Sonotrode 50 is a monolithic block of aluminum 6061 (an alloy of aluminum that includes magnesium and silicon as alloying elements) so that stem portion 52 and cap portion 54 are integrally formed.

Stem portion 52 bears a proximal face 56 (also called "input surface") of sonotrode 50 and has a distal end 58. Sonotrode 50 is acoustically coupled to distal face 18 of transducer 12 through proximal face 56 of sonotrode 50. As will be discussed in greater detail below, stem portion 52 is configured substantially as a stepped taper sonotrode, having a circular cross section perpendicular to sonotrode axis 28, where the proximal part is 2.75 cm long and has a 40 mm diameter while the distal part is 2.15 cm long and has a 20 mm diameter.

Cap portion 54 has a proximally-facing back side 60, a distal working face 62 (also called "contact area" or "output surface") of sonotrode 50 and a periphery 64. Cap portion 54 is substantially a disk have a circular cross section with a 88 mm diameter perpendicular to sonotrode axis 28 and is uniformly 6 mm thick.

Distal end 58 of stem portion 52 meets back side 60 of cap portion 54.

The axial length of sonotrode 50 from proximal face 56 to working face 62 is 55 mm, which is $\lambda L/2$, $\lambda L$ being the wavelength of ultrasonic longitudinal vibrations of the selected ultrasonic frequency of 57.5 kHz for sonotrode 50.

An ultrasound power supply 34 is functionally associated with transducer 12.

For use, working face 62 of sonotrode 50 of device 48 is acoustically coupled with a skin surface (e.g., by direct contact or by indirect contact through a coupling substance, e.g., a liquid or gel), and an AC oscillating at the selected ultrasonic frequency of sonotrode 50 is supplied from ultrasound power supply 34 to drive ultrasonic transducer 12 to generate ultrasonic longitudinal vibrations. The generated ultrasonic longitudinal vibrations propagate in parallel with axis 28 through sonotrode 50 from proximal face 56 to the working face 62. As briefly discussed and as known in the art, a consequence of the configuration of sonotrode 50 to function as an acoustic amplitude transformer for the selected ultrasonic frequency is that the relatively small-amplitude of the longitudinal vibrations at distal face 18 of transducer 12 are transformed to relatively large-amplitude longitudinal vibrations at working face 62 of sonotrode 50.

It has been surprisingly found that when using a device according to the teachings herein, both ultrasonic longitudinal vibrations and ultrasonic transverse vibrations are simultaneously transdermally induced in subcutaneous tissue, both modes of vibrations having sufficient intensity to deliver substantial energy to achieve a desired biological effect, e.g., substantial heating of tissue and substantial disrupting of adipocytes.

A non-trivial goal for simultaneous induction of transverse and longitudinal ultrasonic vibrations in subcutaneous tissue is that the energy delivered by the two modes of vibration be "balanced". It has been surprisingly found that this goal is achieved by a device according to the teachings herein, specifically, that the energy delivered by the two modes of vibration is "balanced", that is to say, during normal use by a body sculpting technician having ordinary skill in the art, the induced ultrasonic transverse vibrations are sufficiently intense to effectively disrupt adipocytes as described in US 2011/0213279 and the simultaneously-induced ultrasonic longitudinal vibrations are sufficiently intense to heat subcutaneous tissue sufficiently to increase the efficacy of the induced ultrasonic transverse vibrations without being so intense as to easily cause potentially catastrophic overheating of bodily tissue (e.g., burns, scarring).

The Inventors' current understanding is that simultaneous transdermal induction of both longitudinal and transverse vibrations in subcutaneous tissue cannot occur through the mechanism described in US 2011/0213279 (generation of ultrasonic shear wave vibrations in a sonotrode cap to induce ultrasonic transverse vibrations in tissue), but apparently through an entirely different and unexpected mechanism. Without wishing to be held to any one theory, it is currently believed that in a device according to the teachings herein, ultrasonic longitudinal vibrations propagate through the sonotrode to the working face, and when applied to a skin surface acoustically coupled with the working face to induce ultrasonic longitudinal vibrations in the subcutaneous tissue in the same or similar fashion as described in the introduction for known sonotrodes. However, due to the particular characteristics of the cap portion of a sonotrode of a device according to the teachings herein, the ultrasonic longitudinal vibrations generated by the ultrasonic transducer act as a line source perpendicular to the cap portion of the sonotrode that is configured as a plate. As a result Lamb waves form in and propagate through the cap portion. (Strictly speaking, the waves formed are cylindrical plate waves, but as the same characteristic equations apply to both Lamb waves and cylindrical plate waves, for convenience the term Lamb waves and cylindrical plate waves will be used here as synonyms.). The Lamb waves lead to ultrasonic flexural vibrations of the cap portion. By some, not yet completely understood mechanism, when the working face is acoustically coupled with skin, the ultrasonic flexural vibrations in the cap portion transdermally induce substantial ultrasonic transverse vibrations in subcutaneous tissue.

Some embodiments of the teachings herein have one or more advantages compared to the teachings of US 2011/0213279 that, depending on the embodiment, include:

a simpler device that requires provision of only a single driving frequency rather than two driving frequencies that are alternately applied through some switching mechanism;

potentially shorter or more effective treatment sessions as a greater proportion of the treatment time is dedicated to inducing adipocyte-disrupting ultrasonic transverse vibrations simultaneously with inducing tissue-heating ultrasonic longitudinal vibrations as opposed to inducing the ultrasonic transverse vibrations only part of the time, alternating with inducing ultrasonic longitudinal vibrations;

potentially shorter or more effective treatment sessions as the ultrasonic transverse vibrations are substantially always induced in or near tissue heated by ultrasonic longitudinal vibrations;

potentially shorter or more effective treatment sessions as some embodiments allow a larger working face that can treat a larger skin surface at any one time compared to the teachings of US 2011/0213279; and potentially shorter or more effective treatment sessions as the use of a device having simultaneous induction of ultrasonic transverse and longitudinal vibrations has been demonstrated to be less sensitive to the skill of the user.

Accordingly, in some embodiments, a device according to the teachings herein is configured to simultaneously transdermally induce substantial ultrasonic transverse vibrations and substantial ultrasonic longitudinal vibrations in a volume of subcutaneous tissue through skin with which the working face is acoustically coupled. In some embodiments, the ultrasonic transducer and the sonotrode are configured so that the volume of material is between 7 cm³ and 56 cm³.

In some embodiments, the substantial transdermally-induced ultrasonic longitudinal vibrations are sufficient to substantially raise the temperature of the volume of hypodermis, in some embodiments raising the temperature of the volume of tissue by not less than 2° C., in some embodiments by not less than 4° C., and in some embodiments by not less than 6° C. For typical treatments it is typically desirable to raise the temperature in the volume of tissue to between 42° C. and 48° C., in some embodiments to between 42° C. and 46° C. and in some embodiments between 42° C. and 45° C.

In some embodiments, the substantial transdermally-induced ultrasonic transverse vibrations are sufficient to initiate a process that leads to irreversible disruption of subcutaneous adipocytes Ultrasonic Transducer As noted above, in some embodiments, a device according to the teachings herein comprises an ultrasonic transducer for the generation of ultrasonic longitudinal vibrations, in FIG. 3 ultrasonic transducer 12 where distal face 18 is the radiating surface of ultrasonic transducer 12.

The ultrasonic transducer of a device according to the teachings herein needs to be able to generate sufficiently powerful ultrasonic longitudinal vibrations to allow practice of the teachings herein. If the transducer is not powerful enough, the device will be ineffective while if the transducer is too powerful, a treated subject may be injured.

Accordingly, an ultrasonic transducer of a device according to the teachings herein is an ultrasonic transducer that, during use, is able to have an ultrasonic power output of the selected frequency of a suitable power, in some embodiments an ultrasonic power output of between 40 Watts and 120 Watts and in some embodiments between 45 Watts and 100 Watts. That said, it has been found that it is preferable that the ultrasonic transducer have an ultrasonic power output of the selected frequency of between 50 Watts and 80 Watts, and even of between 60 Watts and 70 Watts.

Any suitable type of ultrasonic transducer may be used in implementing the teachings herein, for example a pre-stressed Langevin-type ultrasonic transducer. Suitable such transducers are available from a variety of commercial sources.

Acoustic Reflector

In some embodiments, a device according to the teachings herein further comprises an acoustic reflector functionally associated with the ultrasonic transducer through the proximal face of the ultrasonic transducer. In FIG. 3, device 48 comprises an acoustic reflector 16 functionally associated with ultrasonic transducer 12 through proximal face 14. Acoustic reflectors are well-known components in the art commercially available from a variety of sources. Some acoustic reflectors are fluid-filled stainless steel enclosures. In some embodiments such as device 48 depicted in FIG. 3, an acoustic reflector is configured as a portion of a cooling assembly, e.g., includes a cooling fluid inlet 66 and a cooling fluid outlet 68.

Ultrasound Power Supply

As known in the art, an alternating current oscillating at an ultrasonic driving frequency is required to drive an ultrasonic transducer to generate ultrasonic vibrations. Such an alternating current is typically provided by an ultrasound power supply functionally associated with the ultrasonic transducer. Accordingly, in some embodiments a device according to the teachings herein comprises an ultrasound power supply functionally associated with the ultrasonic transducer, configured to provide to the ultrasonic transducer, when activated, an alternating current oscillating at the selected ultrasonic frequency. In FIG. 3, device 48 comprises an ultrasound power supply 34 functionally associated with ultrasonic transducer 12

An ultrasound power supply suitable for implementing the teachings herein is configured to provide an alternating current oscillating at the selected ultrasonic frequency having sufficient power so that the ultrasonic transducer has a desired power output as discussed above. Accordingly, in some embodiments, the ultrasound power supply is configured to provide an alternating current oscillating at the selected ultrasonic frequency with a power so that the ultrasonic transducer has a power output of between 40 Watts and 120 Watts, in some embodiments between 45 Watts and 100 Watts, in some embodiments between 50 Watts and 80 Watts, and in some embodiments even between 60 Watts and 70 Watts.

Sonotrode

As depicted in FIG. 3, sonotrode 50 includes a proximal stem portion 52 defining an axis 28 and a distal cap portion 54.

Selected Ultrasonic Frequency and Acoustic Amplitude Transformer

As noted above, a sonotrode of a device according to the teachings herein is configured to function as an acoustic amplitude transformer for a selected ultrasonic frequency.

The selected ultrasonic frequency is the driving frequency of the ultrasonic transducer, the frequency of the ultrasonic longitudinal vibrations generated by the ultrasonic transducer and the frequency of the ultrasonic longitudinal vibrations transdermally induced in subcutaneous tissue.

The selected ultrasonic frequency is any suitable ultrasonic frequency, in some embodiments between 20 kHz and 150 kHz, and even between 20 kHz and 80 kHz. That said, due to limitations in size of the sub-assembly of the device that includes the transducer and the sonotrode (in some embodiments, a hand-piece that is preferably handheld during use in treating a subject), the requirement that the sonotrode be configured as an acoustic amplitude transformer for the selected ultrasonic frequency and the limited number of materials from which the sonotrode can be made (which limits the speed of sound through the sonotrode to certain values), in some preferred embodiments the selected ultrasonic frequency is between 55 kHz and 70 kHz Length of Sonotrode A person having ordinary skill in the art knows that, in some embodiments, configuration of a sonotrode to function as an acoustic amplitude transformer for a selected ultrasonic frequency includes that the length of the sonotrode from the proximal face of the sonotrode (in FIG. 3, 56) to the distal working face (62) along the sonotrode axis (28) is an integral multiple of $\lambda L/2$, $\lambda L$ being the wavelength of ultrasonic longitudinal vibrations of the selected ultrasonic frequency, which is dependent on the longitudinal speed of sound along the sonotrode axis from the proximal face of the sonotrode to the working face. In FIG. 3, the axial length of sonotrode 50 from proximal face 56 to working face 62 is 55 mm, which is $\lambda L/2$, being the wavelength of ultrasonic longitudinal vibrations of the selected ultrasonic frequency of 57.5 kHz for sonotrode 50.

In some embodiments, the length of the sonotrode is set based on the longitudinal speed of sound through the sonotrode at room temperature (25° C.).

In some embodiments, the length of the sonotrode is set based on the longitudinal speed of sound through the sonotrode to an expected operating temperature (e.g., 36°-40° C.).

That said, in some embodiments the length of a sonotrode from the proximal face of the sonotrode to the distal working face is not less than 50 mm and not more than 300 mm.

Construction and Material of Sonotrode

A sonotrode of a device according to the teachings herein is made using any suitable method. That said, to avoid imperfections, seams and interfaces that could potentially compromise the vibration-transmission properties of the sonotrode, in some embodiments, the cap portion of the sonotrode is integrally formed with the rod portion of the sonotrode.

A sonotrode of a device according to the teachings herein is made of any suitable material. Due to need for low acoustic loss, high dynamic fatigue strength, resistance to cavitation erosion and chemical inertness suitable materials include titanium, titanium alloys, aluminum, aluminum alloys, aluminum bronze or stainless steel. Accordingly, in some embodiments the sonotrode is made of a material selected from the group consisting of titanium, titanium alloys, aluminum, aluminum alloys, aluminum bronze and stainless steel.

Of the listed materials, aluminum and aluminum alloys have an acoustic impedance closest to that of skin, so a sonotrode made of aluminum or aluminum alloys has superior acoustic transmission properties to skin. Accordingly, in some preferred embodiments the sonotrode is made of a material selected from the group consisting of aluminum and aluminum alloys.

In some such embodiments, the working face is coated with aluminum oxide, but such embodiments may leave an aluminum oxide residue on treated skin surfaces so are less preferred. In some embodiments, the working face is coated with an acoustic matching layer (e.g., PVDF or PTFE) on an aluminum oxide layer. Such double layer coating improves the acoustic coupling of the working face with tissue. In such embodiments, the aluminum oxide layer is not more than 75 micrometers thick, not more than 50 micrometers thick, not more than 40 micrometers thick, and even between 5 micrometers and 15 micrometers e.g., 10 micrometers) while the acoustic matching layer applied to the surface of the aluminum oxide layer (e.g., of PVDF or PTFE) is typically 1 to 50 micrometers thick, preferably 5 to 20 micrometers thick.

In some embodiments where a sonotrode is made of aluminum, a hard anodization layer on the working face may give poor results, apparently the hard anodization layer having an acoustic impedance substantially different from that of skin. In contrast, a soft anodization layer on the working face gives acceptable results. Accordingly, in some embodiments the working face of the sonotrode comprises a soft anodization layer, in some embodiments between 5 and 20 micrometers thick, and in some embodiments, between 8 and 12 micrometers thick, e.g., 10 micrometers thick.

Stem Portion

As noted above and seen in FIG. 3, a sonotrode 50 according to the teachings herein includes a narrower proximal stem portion 52 that defines the sonotrode axis 28 and a broader distal cap portion 54. The stem portion 52 bears the proximal face 56 of the sonotrode 50 through which the sonotrode 50 is acoustically coupled to the distal face 18 of the ultrasonic transducer 12. The distal end 58 of the stem portion 52 meets the back side 60 of the cap portion 54.

In preferred embodiments, the stem portion is coaxial with the sonotrode axis. In device 48 depicted in FIG. 3, stem portion 52 is coaxial with sonotrode axis 28.

The stem portion has any suitable cross section perpendicular to the sonotrode axis. In preferred embodiments, the stem portion has a circular cross section perpendicular to the sonotrode axis. In device 48 depicted in FIG. 3, stem portion 52 has a circular cross section perpendicular to sonotrode axis 28.

Taper of Stem Portion

In some embodiments, configuration of a sonotrode to function as an acoustic amplitude transformer for a selected ultrasonic frequency includes that the stem portion is tapered. The term "taper" and variants thereof are used herein as understood by a person in the art of ultrasonic vibrations, that is to say that the cross sectional area of the proximal face is greater than the cross sectional area of the distal portion, and that the cross sectional area of the stem portion does not increase when moving from the proximal face towards the distal portion. As is known to a person having ordinary skill in the art, the ratio of the cross sectional area of the proximal face (A) to the cross sectional area of the distal end of the stem portion (a) determines the magnitude of amplitude amplification of an acoustic amplitude transformer. The most common taper configurations are as depicted in FIG. 2A (linear taper, amplitude amplification is the square root of A/a), FIG. 2B (exponential taper, amplitude amplification is square root of A/a), and FIG. 2C (stepped taper, amplification is A/a). In device 48 depicted in FIG. 3, stem portion 52 has a stepped taper configuration.

The ratio of the cross sectional area of the proximal face (A) to the cross sectional area of the distal end of the stem portion (a) is any suitable ratio. That said, in some preferred embodiments the ratio is such that the magnitude of amplitude amplification of ultrasonic longitudinal vibrations having the selected ultrasonic frequency is not less than 2.5×, not less than 3.0×, not less than 3.5× and even not less than 4.0×. In device 48 depicted in FIG. 3, the diameter of proximal portion 56 is 40 mm twice the diameter of the distal end 58 which is 20 mm, so that the magnitude of the amplitude amplification is 0.0×.

Size of Distal End of Stem Portion

As discussed immediately above, the main determinant of the cross sectional area of the stem portion (when having a circular cross section as depicted in FIG. 3, the diameter) is the configuration of the sonotrode as an acoustic amplitude transformer for the selected ultrasonic frequency.

That said, it is important that the stem portion be sufficiently thick to be robust for use. Accordingly, in some typical embodiments, the cross sectional area of the distal end of the stem portion where the stem portion meets the back side of the cap portion is not less than that of a 5 mm diameter circle (20 mm$^2$), not less than that of a 7 mm diameter circle (38 mm$^2$) and even not less than that of a 9 mm diameter circle (64 mm$^2$). In device 48 depicted in FIG. 3, the diameter of distal end 58 of stem portion 52 where stem portion 52 meets back side 60 of cap portion 64 is 20 mm, accordingly having a cross sectional area of 314 mm$^2$.

It is currently believed that it is preferable that near the cap portion the stem portion be as thin as possible, not only for increased amplitude amplification but also because it is believed that smaller dimensions lead to a more balanced energy distribution between the ultrasonic transverse and longitudinal waves transdermally induced in tissue. Although not wishing to be held to any one theory, it is currently believed that a smaller stem portion allows the cap portion to be "floppier" and therefore more easily subject to flexural vibrations.

Accordingly, in some typical embodiments, the cross sectional area of the distal end of the stem portion where the stem portion meets the back side of the cap portion is not more than that of a 25 mm diameter circle (491 mm$^2$), not more than that of a 23 mm diameter circle (415 mm$^2$) and even not more than that of a 21 mm diameter circle (346 mm$^2$).

Meeting of Stem Portion and Cap Portion

As noted above, the stem portion meets the back side of the cap portion.

In some embodiments, the distal end of the stem portion meets the back side of the cap portion at a right angle, for example, in device 48 depicted in FIG. 3.

In some embodiments, the device further comprises a fillet (an inwardly curved meeting) where the distal end of the stem portion meets the back side of the cap portion, mechanically strengthening the meeting.

In some embodiments, the device further comprises a chamfer (in a cross section that includes the sonotrode axis, a straight line segment that connects the shaft of the stem portion with the back side of the cap portion) where the distal end of the stem portion meets the back side of the cap portion, mechanically strengthening the meeting.

Cap Portion

As noted above and seen in FIG. 3, in some embodiments cap portion 54 has a proximally-facing back side 60, a distal working face 62 of sonotrode 50 and a periphery 64, wherein distal end 58 of stem portion 52 meets back side 60 of cap portion 54, and wherein where distal end 28 of stem portion 52 meets back side 60 of cap portion 54, the cross sectional area of cap portion 54 perpendicular to sonotrode axis 28 is not less than 4 times greater than the cross sectional area of distal end 28 of stem portion 52 perpendicular to the sonotrode axis 28.

In preferred embodiments, the cap portion is coaxial with the sonotrode axis. In device 48 depicted in FIG. 3, cap portion 54 is coaxial with sonotrode axis 28.

The cap portion has any suitable cross section perpendicular to the sonotrode axis. In preferred embodiments, the cap portion has a circular cross section perpendicular to the sonotrode axis. In device 48 depicted in FIG. 3, cap portion 54 has a circular cross section perpendicular to sonotrode axis 28.

Working Face and Back Side

The working face has any suitable shape perpendicular to the sonotrode axis. In preferred embodiments, the working face is circular. In device 48 depicted in FIG. 3, working face 62 has a circular shape perpendicular to sonotrode axis 28.

In some embodiments, not less than 70% of the surface area of the working face is planar and perpendicular to the sonotrode axis. In some such embodiments, not less than 80%, not less than 90% and even not less than 95% of the surface area of the working face is planar and perpendicular to the sonotrode axis. In device 48 depicted in FIG. 3, more than 95% of the surface area of working area 62 is planar and perpendicular to sonotrode axis 28.

In some embodiments, not less than 70% of the surface area of the back side is planar and perpendicular to the sonotrode axis. In some such embodiments, not less than 80%, not less than 90% and even not less than 95% of the surface area of the back side is planar and perpendicular to the sonotrode axis. In device 48 depicted in FIG. 3, more than 95% of the surface area of back side 60 is planar and perpendicular to sonotrode axis 28.

In some preferred embodiments, not less than 70% of the surface area of both the working face and of the back side are planar and mutually parallel. In some such embodiments, not less than 80%, not less than 90% and even not less than 95% of the surface area of both the working face and of the back side are planar mutually parallel. In some preferred embodiments, the planar and mutually parallel portions of the working face and of the back side are also perpendicular to the sonotrode axis. Without wishing to be held to any one theory, it is currently believed that when a substantial portion of both the working face and the back side are planar and mutually parallel, the cap portion more easily allows propagation of Lamb Waves, and the cap portion is "floppier" and therefore more easily subject to flexural vibrations. In device 48 depicted in FIG. 3, more than 95% of the surface area of both working face 62 and back side 60 are planar, mutually parallel and perpendicular to sonotrode axis 28.

Smoothness of Working Face and Back Side

As discussed hereinabove in the introduction, the teachings of US 2011/0213279 are preferably implemented when the working face of a sonotrode includes transverse-wave transferring ridges.

In contrast, it has been found that when implementing the teachings herein, it is preferable, and in some embodiments critical, that both the working face and the back side be smooth and featureless. It was found that 200 micrometer high concentric rings on an otherwise smooth working face were relatively ineffective in inducing Without wishing to be held to any one theory, it is currently believed that surface variations disrupt the formation and/or propagation of Lamb Waves and/or flexural vibrations.

Accordingly, in some embodiments, the planar part of the working face of the sonotrode is smooth.

In some embodiments, the planar part of the working face of the sonotrode is devoid of surface variations greater than 200 micrometers, 100 micrometers, 50 micrometers and even 20 micrometers.

In some embodiments, the planar part of the back side of the cap portion is smooth.

In some embodiments, the planar part of the back side of the cap is devoid of surface variations greater than 200 micrometers, 100 micrometers, 50 micrometers and even 20 micrometers.

In device 48 depicted in FIG. 3, the planar parts of both working face 62 and back side 60 are smooth and have no surface variations greater than 20 micrometers.

Thickness of Cap Portion

As used herein, the thickness of the cap portion is defined as the longitudinal dimension along the sonotrode axis. In general, it is desirable that the cap portion be as thin as possible, allowing the cap portion to be "floppier". At the same time, it is necessary that the cap portion be thick enough to be sufficiently robust.

In some embodiments, the thickness of the cap portion is less than or equal to $\lambda L/10$, $\lambda L$ being the wavelength of ultrasonic longitudinal vibrations of the selected ultrasonic frequency.

In some embodiments, the cap portion is not less than 2 mm, not less than 3 mm, not less than 4 mm and even not less than 5 mm thick.

In some embodiments, the cap portion is not more than 10 mm, not more than 9 mm, not more than 8 mm and even not more than 7 mm thick.

In device 48 depicted in FIG. 3, cap portion 54 is 6 mm thick.

Periphery

The periphery of the cap portion of a sonotrode of a device according to the teachings herein is any suitable periphery. That said, in some embodiments the periphery, when viewed from the side is a straight line. That said, in some embodiments the periphery, when viewed from the side is a straight line parallel to the sonotrode axis. In device 48 depicted in FIG. 3, when viewed from the side, periphery 64 of ring portion is a straight line parallel to sonotrode axis 28. Without wishing to be held to any one theory, it is currently believed that when the periphery is a straight line, especially a straight line parallel to the sonotrode axis, Lamb Waves more easily propagate in the cap portion.

The edges of the periphery where the periphery meets either the back side or the working face are of any suitable configuration.

In some embodiments, an edge of where the periphery of the cap portion meets the back side, the working face or both the back side and the working face is a right angle, that is to say the back side/working face intersect the periphery at a right angle. For example, in device 48 depicted in FIG. 3, the edges where periphery 64 meets back side 60 are right angles.

A disadvantage of right angle edges, especially of the working face, is that these may scrape or be otherwise uncomfortable to a person. Accordingly, in some embodiments, an edge of where the periphery of the cap portion meets the back side, the working face or both the back side and the working face is not a right angle (e.g., is beveled or rounded). For example, in device 48 depicted in FIG. 3, the edges where periphery 64 meets working face 62 are rounded.

Cylindrical Cap Portion

As is clear to a person having ordinary skill in the art, in some preferred embodiments such as depicted in FIG. 3, where not less than 90% of both the working face and the back side of the cap portion are planar and perpendicular to the sonotrode axis, and where the periphery of the cap portion, when viewed from the side is a straight line parallel to the sonotrode axis, a side cross section of the cap portion is a rectangle and the cap portion is substantially a right cylinder (excluding the edges, that may be rounded or beveled). It is currently believed that such embodiments are preferred for providing the most balanced transdermal induction of ultrasonic transverse and longitudinal waves in subcutaneous tissue.

Size of Cap Portion

The size of the cap portion (in terms of cross sectional area perpendicular to the sonotrode axis, or equivalently, the diameter of a circular cap portion) is any suitable size.

It is currently believed that it advantageous that the cap portion and working face be as large as possible as this allows the amplitude of flexural vibrations to be as large as possible and, all other things being equal, a larger cap portion is "floppier". On the other hand, a large cap portion with a working face that is too large to make adequate contact with a skin surface to be treated is presumably unsuitable for efficiently inducing transverse ultrasonic vibrations in subcutaneous tissue.

Accordingly, in some embodiments the area of a cross section perpendicular to the sonotrode axis of the cap portion through the longitudinal center of the cap portion (indicated by line 70 in FIG. 3) is not more than that of a 150 mm diameter circle (17700 $mm^2$), not more than that of a 130 mm diameter circle (13300 $mm^2$) and even not more than that of a 100 mm diameter circle (7850 $mm^2$). In device 48 depicted in FIG. 3, the diameter of cap portion 54 is 88 mm, so that the area of a cross section perpendicular to sonotrode axis 28 of cap portion 54 through the longitudinal center 70 of cap portion 54 is 6080 $mm^2$.

As noted above, in some preferred embodiments, where the distal end (58 in FIG. 3) of the stem portion (52) meets the back side (60) of the cap portion (54) the cross sectional area of the cap portion (54) perpendicular to the axis is not less than 4 times greater than the cross sectional area of the distal end (58) of the stem portion (52) perpendicular to the sonotrode axis (28). Without wishing to be held to any one theory, it is currently believed that a smaller cap portion will be insufficiently "floppy" for efficient flexural vibration. In some embodiments, the cross sectional area of the cap portion is even larger, being not less than 6 times, not less than 8 times, not less than 10 times, not less than 12 times, not less than 14 times and even not less than 16 times greater than the cross sectional area of the distal end of the stem portion. In device 48 depicted in FIG. 3, the diameter of cap portion 54 is 88 mm and the diameter of distal end 58 of stem portion 52 is 20 mm, so that where distal end 58 of stem portion 52 meets back side 60 of cap portion 54 the cross sectional area of cap portion 54 perpendicular to the sonotrode axis 28 is 19.4 times the cross sectional area of distal end 58.

Cooling Assembly

As is known to a person having ordinary skill in the art, during operation of an ultrasonic transducer an associated sonotrode may be heated to a temperature that makes skin contact with the working face of the sonotrode uncomfortable or even harmful. Additionally, heating of subcutaneous tissue may lead to excessive heating of the skin.

To reduce the incidence of such undesirable effects when the device is used, in some embodiments the device is configured to actively cool at least a portion of the working face. To this end, in some embodiments, a device further comprises a cooling assembly configured, when activated, to cool at least a portion of the working face, directly or indirectly (e.g., by cooling a distal part of the transducer or the sonotrode which is in thermal communication with the working face. In some embodiments, a device further comprises cooling-fluid channels in thermal communication with the working face, e.g., the cooling-fluid channels are in thermal communication with the sonotrode.

During use of the device, such cooling-fluid channels can be functionally associated with an appropriately configured cooling device or cooling assembly that drives a cooling fluid through the cooling-fluid channels, thereby cooling the working face. In some embodiments, the device further comprises a cooling assembly functionally associated with the cooling-fluid channels configured, when activated, to drive a cooling fluid through the cooling-fluid channels, thereby cooling the working face.

Construction and use of such a cooling assembly is described in U.S. Pat. No. 9,545,529 of the Applicant, which is included by reference as if fully set forth herein.

Method of Treatment Using the Device

A device according to the teachings herein may be used in implementing a method of transdermally treating subcutaneous fat according to the teachings herein. According to an aspect of some embodiments of the teachings herein, there is provided a method of transdermally treating subcutaneous fat comprising:
  i. providing a device according to the teachings herein, wherein the ultrasonic transducer is functionally associated with an ultrasound power supply;
  ii. for a treatment event having a duration, maintaining the working face acoustically coupled with a skin surface while the ultrasound power supply is activated to supply a driving current having the selected ultrasonic frequency to the ultrasonic transducer,
thereby simultaneously transdermally inducing both:
    ultrasonic longitudinal vibrations (perpendicular to the skin surface) sufficient to convey sufficient energy to substantially heat subcutaneous tissue; and
    ultrasonic transverse vibrations (parallel to the skin surface) in subcutaneous tissue to convey sufficient energy to disrupt adipocytes in the subcutaneous tissue.

Typically, the method is non-invasive, that is to say the skin surface remains intact, and is not punctured or otherwise penetrated. In some embodiments, the method is a non-surgical method, performed without breaking the skin. Embodiments of the method are performed by any suitable person, including medical personnel but typically aesthetic technicians such as beauticians.

In some embodiments, the simultaneous inducing of ultrasonic longitudinal vibrations and ultrasonic transverse vibrations initiates a process leading to a reduction of the amount of subcutaneous fat in proximity to the skin surface.

In some embodiments, the ultrasonic longitudinal vibrations convey sufficient energy to raise the temperature of the subcutaneous tissue, as discussed above with reference to the device of the teachings herein.

In some embodiments, a treatment session comprises one or more treatment events. During a treatment session (typically between 15 minutes and 60 minutes), an operator uses the device to transdermally treating subcutaneous fat of a subject. During each treatment event, the operator typically slides the working face over an area of the skin of the subject, ensuring homogeneous heating of the subcutaneous tissue in proximity of the area of the skin by the action of the induced longitudinal vibrations.

A single treatment event is of any suitable duration. In some embodiments, a single treatment event has a duration of not less than 30 seconds.

In some embodiments, the ultrasound power supply is continuously activated to supply the driving current throughout the treatment event.

In some embodiments, the ultrasound power supply is intermittently activated during the treatment event.

In some embodiments, during the treatment event, the driving current having the selected frequency is the only driving current supplied to the ultrasonic transducer.

In some embodiments, the working face is directly acoustically coupled with a skin surface.

In some embodiments, the working face is indirectly acoustically coupled with a skin surface through a fluid (e.g., petroleum jelly, or an impedance-matching material such as an ultrasound gel (e.g., Graham-Field Ultrasound Gel, GF Health Products Inc., Atlanta, Ga., USA).

In some embodiments, during the treatment event, maintaining a temperature of the working face at not more than 42° C. In some such embodiments, maintaining the temperature is performed by operating a cooling assembly that is part of the device.

In some embodiments a portion of the skin surface of the subject is actively cooled.

In some embodiments, the method further comprises, during a treatment event, cooling a portion of a skin surface proximal to the working face, in some embodiments, thereby effecting cooling of a portion of a skin surface proximal to the working face. In some such embodiments, the working face is cooled, for example by the passage of a cooling fluid in proximity thereto (for example near or through the sonotrode), to effect cooling of the portion of the skin surface.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:
1. A device suitable for treating subcutaneous adipose tissue, comprising:
  a. an ultrasonic transducer for generation of ultrasonic vibrations having a proximal face and a distal face; and b. a sonotrode including a narrower proximal stem portion defining a sonotrode axis and a broader distal cap portion,
wherein said stem portion has a distal end and bears a proximal face of said sonotrode, said sonotrode acoustically coupled to said distal face of said ultrasonic transducer through said proximal face of said sonotrode,
wherein said cap portion has a proximally-facing back side, a distal working face of said sonotrode and a periphery,
wherein said distal end of said stem portion meets said back side of said cap portion,
wherein, where said distal end of said stem portion meets said back side of said cap portion, a cross sectional area of said cap portion perpendicular to said sonotrode axis is not less than 4 times greater than a cross sectional area of said distal end of said stem portion perpendicular to said sonotrode axis;
wherein said sonotrode is configured as an acoustic amplitude transformer for a selected ultrasonic frequency; and
wherein a cross sectional area of said distal end of said stem portion where said stem portion meets said back side of said cap portion is not less than that of a 5 mm diameter circle (20 mm$^2$) and not more than that of a 25 mm diameter circle (491 mm$^2$).

2. The device of claim 1, configured to simultaneously transdermally induce ultrasonic transverse vibrations and ultrasonic longitudinal vibrations in a volume of subcutaneous tissue through skin with which said working face is acoustically coupled.

3. The device of claim 1, further comprising an ultrasound power supply functionally associated with said ultrasonic transducer, configured to provide to said ultrasonic transducer, when activated, an alternating current oscillating at said selected ultrasonic frequency.

4. The device of claim 1, wherein said stem portion of said sonotrode is tapered, wherein said tapering is such that a ratio of a cross sectional area of said proximal face of said sonotrode to a cross sectional area of said distal end of said stem portion is such that a magnitude of amplitude amplification of ultrasonic longitudinal vibrations having said selected ultrasonic frequency is not less than 2.5 X.

5. The device of claim 1, wherein not less than 70% of a surface area of said working face is planar and perpendicular to said sonotrode axis.

6. The device of claim 1, wherein not less than 70% of a surface area of the back side is planar and perpendicular to said sonotrode axis.

7. The device of claim 1, wherein not less than 70% of a surface area of both said working face and of said back side are planar and mutually parallel.

8. The device of claim 7, wherein portions of said working face and of said back side that are planar and mutually parallel are perpendicular to said sonotrode axis.

9. A device suitable for treating subcutaneous adipose tissue, comprising:
a. an ultrasonic transducer for generation of ultrasonic vibrations having a proximal face and a distal face; and
b. a sonotrode including a narrower proximal stem portion defining a sonotrode axis and a broader distal cap portion,
wherein said stem portion has a distal end and bears a proximal face of said sonotrode, said sonotrode acoustically coupled to said distal face of said ultrasonic transducer through said proximal face of said sonotrode,
wherein said cap portion has a proximally-facing back side, a distal working face of said sonotrode and a periphery,
wherein said distal end of said stem portion meets said back side of said cap portion,
wherein, where said distal end of said stem portion meets said back side of said cap portion, a cross sectional area of said cap portion perpendicular to said sonotrode axis is not less than 4 times greater than a cross sectional area of said distal end of said stem portion perpendicular to said sonotrode axis;
wherein said sonotrode is configured as an acoustic amplitude transformer for a selected ultrasonic frequency; and
wherein a planar part of said working face of said sonotrode is devoid of surface variations greater than 200 micrometers and a planar part of said back side of said cap portion of said sonotrode is devoid of surface variations greater than 200 micrometers.

10. The device of claim 1, wherein said cap portion is not less than 2 mm and not more than 10 mm thick.

11. The device of claim 1, wherein said periphery, when viewed from a side, is a straight line, wherein said straight line is parallel to said sonotrode axis.

12. The device of claim 1, wherein said cap portion is a right cylinder.

13. The device of claim 1, wherein an area of a cross section perpendicular to said sonotrode axis of said cap portion is not more than that of a 150 mm diameter circle (17700 mm$^2$).

14. The device of claim 1, wherein where said distal end of said stem portion meets said back side of said cap portion, a cross sectional area of said cap portion perpendicular to said axis is not less than 6 times greater than a cross sectional area of said distal end of said stem portion perpendicular to said sonotrode axis.

15. A method of transdermally treating subcutaneous fat comprising:
providing a device according to claim 1, wherein said ultrasonic transducer is functionally associated with an ultrasound power supply;
for a treatment event having a duration, maintaining said working face acoustically coupled with a skin surface while said ultrasound power supply is activated to supply a driving current having said selected ultrasonic frequency to said ultrasonic transducer, thereby simultaneously transdermally inducing both:
ultrasonic longitudinal vibrations sufficient to convey energy to heat subcutaneous tissue; and
ultrasonic transverse vibrations in subcutaneous tissue to convey sufficient energy to disrupt adipocytes in the subcutaneous tissue.

16. The device of claim 1, said cap portion not less than 2 mm and not more than 10 mm thick.

* * * * *